US008905298B2

(12) United States Patent
Paintin

(10) Patent No.: US 8,905,298 B2
(45) Date of Patent: Dec. 9, 2014

(54) TRANSACTIONS WITH IMAGING ANALYSIS

(75) Inventor: Scott Paintin, Littleton, CO (US)

(73) Assignee: The Western Union Company, Englewood, CO (US)

( * ) Notice: Subject to any disclaimer, the term of this patent is extended or adjusted under 35 U.S.C. 154(b) by 733 days.

(21) Appl. No.: 12/494,585

(22) Filed: Jun. 30, 2009

(65) Prior Publication Data
US 2010/0332390 A1 Dec. 30, 2010

(51) Int. Cl.
G06Q 20/40 (2012.01)
G06Q 20/10 (2012.01)
G06Q 20/04 (2012.01)

(52) U.S. Cl.
CPC ............ G06Q 20/10 (2013.01); G06Q 20/40 (2013.01)
USPC ............. 235/379; 235/380; 235/371; 705/43; 705/44

(58) Field of Classification Search
CPC ....... G06Q 20/40; G06Q 20/10; G06Q 20/04; G06Q 20/1085; G06Q 20/042; G06Q 19/20
USPC .................. 705/26.35, 39, 43, 44, 75, 64, 67; 382/100, 115, 139; 235/379, 380, 383, 235/454, 381; 455/411; 713/186, 182; 434/236; 607/2; 725/10, 16; 706/12, 706/45; 600/13, 300
See application file for complete search history.

(56) References Cited

U.S. PATENT DOCUMENTS

| | | | | |
|---|---|---|---|---|
| 5,557,518 A | * | 9/1996 | Rosen | 705/69 |
| 5,675,662 A | | 10/1997 | Deaton et al. | |
| 6,827,260 B2 | * | 12/2004 | Stoutenburg et al. | 235/380 |
| 6,941,274 B1 | * | 9/2005 | Ramachandran et al. | 705/26.35 |
| 7,003,493 B2 | * | 2/2006 | Weichert et al. | 705/39 |
| 7,213,744 B2 | * | 5/2007 | Michelsen et al. | 235/379 |
| 7,349,566 B2 | * | 3/2008 | Jones et al. | 382/139 |
| 7,818,423 B1 | * | 10/2010 | Philyaw | 709/225 |
| 2001/0001877 A1 | * | 5/2001 | French et al. | 713/182 |
| 2002/0010684 A1 | * | 1/2002 | Moskowitz | 705/75 |
| 2002/0056043 A1 | | 5/2002 | Glass | |
| 2002/0166891 A1 | | 11/2002 | Stoutenburg et al. | |

(Continued)

FOREIGN PATENT DOCUMENTS

| | | | | | |
|---|---|---|---|---|---|
| JP | 2002041814 | * | 8/2003 | | G06F 17/60 |
| JP | 2003242391 | * | 8/2003 | | G06F 17/60 |

OTHER PUBLICATIONS

International Search Report and Written Opinion of PCT/US2010/027669 mailed on May 17, 2010, 9 pages.

(Continued)

*Primary Examiner* — Barbara Amelunxen
(74) *Attorney, Agent, or Firm* — Kilpatrick Townsend & Stockton LLP

(57) ABSTRACT

A money transfer system with imaging. The system includes a first money transfer terminal and an imaging device. The imaging device is configured to acquire a first set of imaging information of a user. The system also includes a host computer system, configured to receive at least a portion of the first set of financial transaction information and at least a portion of the first set of imaging information. The system also includes a previous transaction database, an external database, and a decision maker terminal. The system also includes a second money transfer terminal and a second imaging device. The second imaging device is configured to acquire a second set of imaging information of the second user.

4 Claims, 7 Drawing Sheets

(56) References Cited

U.S. PATENT DOCUMENTS

| | | |
|---|---|---|
| 2003/0063772 A1* | 4/2003 | Smith et al. .................. 382/100 |
| 2003/0149662 A1 | 8/2003 | Shore |
| 2004/0024700 A1 | 2/2004 | Petigny |
| 2004/0169722 A1* | 9/2004 | Pena ........................ 348/14.01 |
| 2004/0205023 A1* | 10/2004 | Hafer et al. .................... 705/43 |
| 2004/0215558 A1 | 10/2004 | Morales et al. |
| 2004/0260649 A1* | 12/2004 | Kagehiro et al. ............... 705/43 |
| 2005/0079474 A1* | 4/2005 | Lowe .......................... 434/236 |
| 2005/0160052 A1* | 7/2005 | Schneider et al. ............. 705/67 |
| 2005/0238208 A1* | 10/2005 | Sim .............................. 382/115 |
| 2005/0256539 A1* | 11/2005 | George et al. .................... 607/2 |
| 2005/0289582 A1* | 12/2005 | Tavares et al. .................. 725/10 |
| 2006/0006224 A1* | 1/2006 | Modi ........................... 235/379 |
| 2006/0160525 A1* | 7/2006 | Watanabe .................... 455/411 |
| 2007/0084911 A1* | 4/2007 | Crowell ....................... 235/379 |
| 2007/0112710 A1* | 5/2007 | Drane et al. .................... 706/45 |
| 2007/0113099 A1* | 5/2007 | Takikawa et al. ............. 713/186 |
| 2007/0117073 A1* | 5/2007 | Walker et al. ................. 434/236 |
| 2007/0175998 A1* | 8/2007 | Lev ............................... 235/454 |
| 2007/0187494 A1* | 8/2007 | Hanna .......................... 235/383 |
| 2007/0198432 A1* | 8/2007 | Pitroda et al. .................... 705/64 |
| 2007/0208662 A1* | 9/2007 | Jeronimus et al. ............. 705/44 |
| 2008/0004519 A1* | 1/2008 | Theriault ...................... 600/410 |
| 2008/0065468 A1* | 3/2008 | Berg et al. ........................ 705/10 |
| 2008/0097186 A1* | 4/2008 | Biglieri et al. ................ 600/407 |
| 2008/0241839 A1* | 10/2008 | Potkin et al. ..................... 435/6 |
| 2008/0243690 A1 | 10/2008 | Paintin et al. |
| 2008/0253621 A1* | 10/2008 | Connell et al. ................ 382/115 |
| 2008/0290154 A1* | 11/2008 | Barnhardt et al. ............. 235/379 |
| 2009/0099983 A1* | 4/2009 | Drane et al. .................... 706/12 |
| 2009/0147990 A1* | 6/2009 | Lev ............................... 382/100 |
| 2009/0192938 A1* | 7/2009 | Amos ............................. 705/43 |
| 2009/0266880 A1* | 10/2009 | Gustin et al. .................. 235/379 |
| 2009/0270692 A1* | 10/2009 | Hyde et al. .................... 600/301 |
| 2010/0063368 A1* | 3/2010 | Leuthardt et al. ............ 600/301 |
| 2010/0113863 A1* | 5/2010 | George et al. .................... 600/13 |
| 2010/0226547 A1* | 9/2010 | Criminisi et al. ............. 382/128 |
| 2010/0250375 A1 | 9/2010 | Diehl |
| 2010/0299517 A1* | 11/2010 | Jukic et al. .................... 713/150 |
| 2011/0184247 A1* | 7/2011 | Contant et al. ................ 600/300 |
| 2012/0047525 A1* | 2/2012 | Campagna et al. ............. 725/16 |

OTHER PUBLICATIONS

International Search Report and Written Opinion of PCT/US2010/039243 mailed on Aug. 20, 2010, 11 pages.

* cited by examiner

TRANSACTIONS WITH IMAGING ANALYSIS

CROSS-REFERENCES TO RELATED APPLICATIONS

This Application is a non-provisional application. It is related to U.S. patent application Ser. No. 12/409,937, filed on Mar. 24, 2009, entitled "Consumer Due Diligence For Money Transfer Systems And Methods." This Application hereby incorporates by reference the content of the aforementioned application in its entirety and for all purposes.

BACKGROUND OF THE INVENTION

Embodiments of the present invention relate generally to imaging, and, in particular, to the analysis of imaging information associated with a money transfer client.

Money transfers present a convenient way to quickly transfer monetary funds over great distances. These transfers allow, for example, a sender to pay cash to an agent of a money transfer business and specify to whom the money will be transferred. The recipient may take distribution of the money, that may occur almost instantaneously, at the same or a different agent location. The agent location where the recipient takes distribution of the money may be in a different city, state, or country than the location from which the sender transmitted the funds. The ability to send large and small amounts of money, including cash, quickly over great distances naturally results in a small percentage of users attempting to exploit such a system for illicit purposes. Further, it may be possible that while the sender realizes the money will be used for illicit purposes, the initial recipient may be unaware the money is intended for such purposes. The reverse situation also may be true: the sender believing she is participating in a legitimate transaction, unaware of the unlawful intentions of the recipient. Of course, in some instances, both parties may be aware of the illegal nature of their transaction.

This minority of users may attempt to use the system to transfer drug money, money for terrorist activities, money to fund gang wars, or countless other illegal or immoral purposes. Further, these users may attempt to conceal the fact that they are using the money transfer system for illicit purposes, making it harder to detect and prevent the transaction. Currently, information that may be collected during a money transfer may be information necessary to identify the recipient and information required by law. Gathering more information on the sender and/or on the recipient, such as their facial expressions, state of mind or current mood, may allow for a more accurate determination of whether the sender, recipient, or both are attempting to use the money transfer system for illicit purposes. This invention serves to remedy these and other problems.

BRIEF SUMMARY OF THE INVENTION

Devices, systems, and methods are described for a novel money transfer architecture. In some embodiments, a money transfer system is described. The money transfer system includes a first money transfer terminal. The first money transfer terminal may be configured to receive financial transaction information from a user and to receive imaging information from a first imaging device. The financial transaction information may include an amount of funds, an intended recipient of the funds, and a location for pick-up of the funds. Financial transaction information may include a control number, such as a transaction identifier, personal information of the sender and/or recipient (e.g. name, address, telephone number, and social security number), loyalty information, and/or payment or payout information such as the account number, routing number, Personal Identification Number ("PIN"), Card Verification Value ("CVV"), etc. At least a portion of the financial information and the imaging information may be transferred to a host computer system. The imaging device may be configured to acquire imaging information of the user and communicates with the first money transfer terminal. The host computer system may be communicatively coupled with a previous transaction database and an external database. The previous transaction database includes financial information and imaging information for a plurality of users, user types, or both. The external database includes imaging information for a plurality of persons, person types, or both. The decision-maker terminal communicates with the host system, displays at least a portion of the financial transaction information and imaging information. The decision maker terminal may receive a decision from a decision maker. The system may further include a second money transfer terminal and a second imaging device. The second money transfer terminal may be configured to disburse at least a portion of the amount of funds, and transmit at least a portion of imaging information on the recipient to the host system. Such an embodiment allows the user sending funds, and the recipient of the funds to be evaluated prior to funds being released.

In some embodiments, the money transfer system includes a money transfer terminal, a user imaging device, and a host computer system. The money transfer terminal may be configured to receive financial transaction information from a user and interface with the host computer system. The user imaging device may be configured to acquire an image of the user. The host computer system may be configured to receive financial transaction information transmitted from the money transfer terminal. In some embodiments, at least a portion of the user information collected by the user imaging device may be transmitted to the host computer system. In some embodiments the imaging device may be a magnetic imaging machine.

In some embodiments of the invention, a method of processing a money transfer may be present. The method provides a money transfer system that includes a money transfer terminal, an imaging device, and a host computer system. The money transfer terminal may be configured to receive financial information from a user. The imaging device may be configured to acquire imaging information of the user. The host computer system may be communicatively coupled with the imaging device and the money transfer terminal. The method also includes receiving financial transaction information at a money transfer terminal from a user, transmitting financial transaction information from the money transfer terminal to the host computer system. The method also includes receiving imaging information associated with the user from the imaging device at the host computer system, and evaluating the imaging information and the financial transaction information.

In some embodiments of the invention, a user may be prompted for more information based at least in part on the imaging information collected from the user. In some embodiments of the invention, the imaging device may be a functional magnetic resonance imaging machine.

In some embodiments of the invention, a method of approving a money transfer initiated (e.g. send a money transfer or receive a money transfer) by a user may be present. The method includes providing a money transfer system, the money transfer system includes a money transfer terminal, an imaging device, and a host computer system. The money transfer terminal may be configured to receive financial information from a user. The imaging device may be configured to acquire imaging information of the user. The host computer system may be communicatively coupled with the imaging device and the money transfer terminal. The method further includes receiving financial transaction information regarding the user at the host computer system from the money transfer terminal, wherein the financial transaction information includes a recipient, alternatively referred to as a target party. The method also includes receiving imaging information regarding the user at the host computer system from the imaging device; accessing a database stored on a computer-readable medium at the host computer system, wherein the database includes imaging information associated with a plurality of persons; comparing the imaging information received from the imaging device to the imaging information stored in the database; and determining whether to approve the money transfer, wherein the determination may be based at least in part on the imaging information received from the imaging device. This allows the imaging information gathered from the user to be evaluated before approval of the money transfer.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

DETAILED DESCRIPTION OF THE INVENTION

Figure 1:
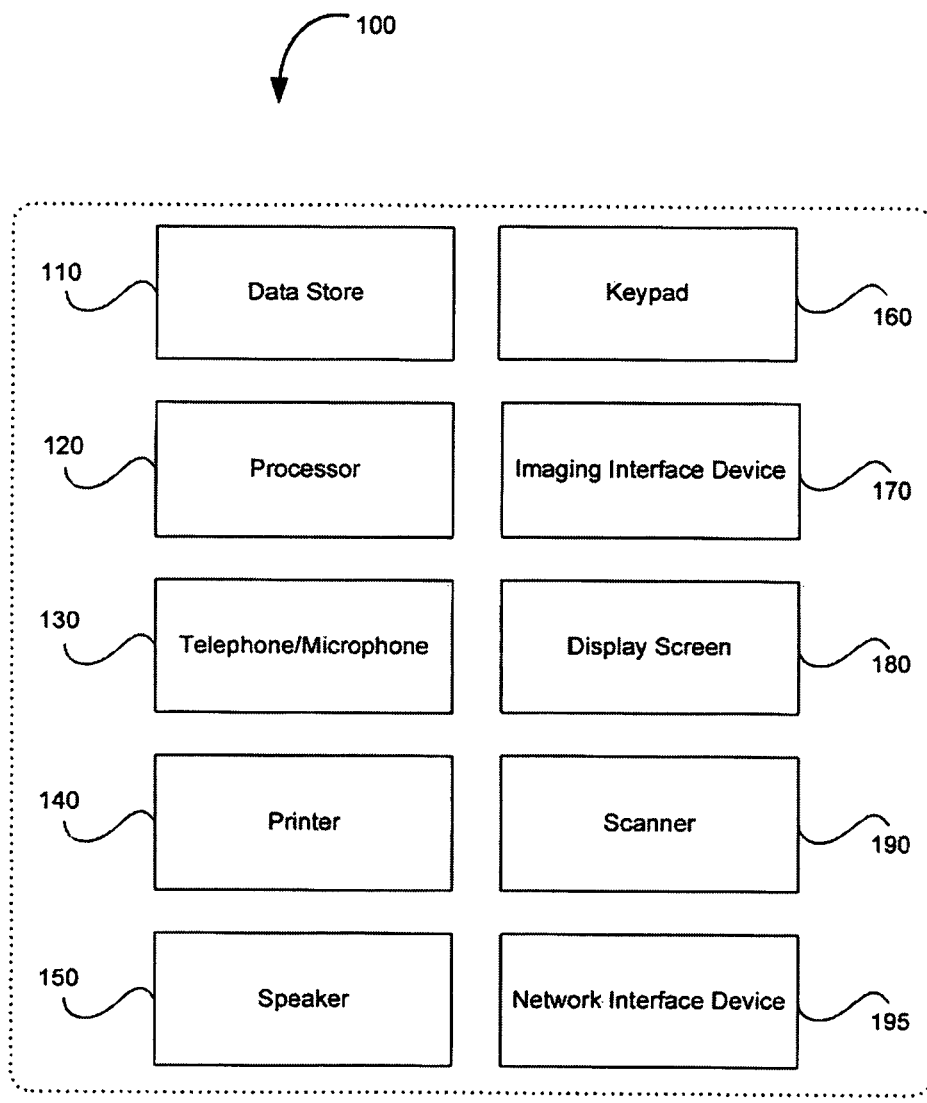
FIG. 1 is a simplified block diagram of an embodiment of a money transfer terminal.

Devices, systems, and methods are described for the implementation of a novel architecture for determining whether a money transfer should be allowed, blocked, or further analyzed. Imaging information of a person sending funds via a money transfer system (a "sender"), gathered by an imaging device, may be analyzed for certain traits, patterns, clues, or other evidence as to the mindset, intentions, or motives of the sender. This information may be used, at least in part, to determine whether to allow, block, or gather further information on the money transfer. A similar analysis may be conducted on the recipient of funds (a "recipient"), as to whether the transaction should be allowed, blocked, or further analyzed.

This description provides example embodiments only, and is not intended to limit the scope, applicability, or configuration of the invention. Rather, the ensuing description of the embodiments will provide those skilled in the art with an enabling description for implementing embodiments of the invention. Various changes may be made in the function and arrangement of elements without departing from the spirit and scope of the invention.

Thus, various embodiments may omit, substitute, or add, various procedures or components as appropriate. For instance, it should be appreciated that in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner.

It should also be appreciated that the following systems, methods, and software may individually or collectively be components of a larger system, wherein other procedures may take precedence over or otherwise modify their application. Also, a number of steps may be required before, after, or concurrently with the following embodiments.

Further, the ensuing description details imaging devices, systems, and methods applied to money transfers. This is meant for example purposes only, and does not serve as a limitation on the applicability of the invention. Those with skill in the art will recognize that similar devices, methods and systems may be applied to bank-based transactions and merchant based transactions (e.g. for fraud prevention, or as a method of placing an order and/or making a payment). Further, such a system may be applicable to many government functions, such as identity verification for the issuing of an identification card, such as a driver's license, social security card, and green card. Moreover, such devices, methods, and systems may be used for determining eligibility for benefits, such as unemployment benefits and social security disability benefits (e.g., determining if an applicant is truly unemployed or disabled so as to prevent or minimize fraudulent claims). In some embodiments, a data collection system is used to practice the invention. The data collection system may include an input terminal (e.g., a point of sale device) for receiving user information (e.g., order information, financial transaction information, name, telephone number, home address, ship-to address, etc.). The data collection system may further include an imaging device for acquiring an image of a user. The input terminal and the imaging device may transmit information to a host computer. The host computer may include or be connected to one or more internal or external databases. The host computer may compare the user information and/or the image of the user to imaging information stored in a database to determine, at least in part, whether to approve a transaction. In some embodiments, the input terminal and the imaging device are the same. Throughout the application, reference to money transfer terminals may instead be considered a reference to input terminals, a reference to a money transfer system may instead be considered a reference to a data collection system, and a reference to send funds (or language of similar import) may instead be considered a reference to purchasing goods or services.

In some money transfer systems, it is desirable to understand the intentions of a user, who may be either a sender or recipient of funds. For example, a person holding a sum of cash may wish to transfer his money to a person to buy automatic weapons for a gang. This person, most likely, will attempt to conceal his illegal goal. A money transfer system having the ability to accurately determine a sender's or recipient's motives, mindset, or intentions may assist in preventing money transfers for illegal purposes.

Such a money transfer system may include a network of money transfer terminals that can communicate to a host money transfer system. This may allow a sender to send funds from one money transfer terminal to a recipient at another money transfer terminal. The sender and/or agent/clerk may input transaction information to a money transfer terminal. Throughout the application, reference to an agent or clerk also may include reference to a representative, such as a call center representative that makes or receives telephone calls for or on behalf of a money transmitter or other company. The information may include pieces of information such as: the sender's name, the sender's address, the sender's phone number, the sender's loyalty number, the sender's account number, the amount to be sent, the form the funds will be paid to the money transfer operator in (such as cash, check, credit, or debit, etc.), the recipient's name, the recipient's address, the recipient's account and/or routing number, the form the funds are to be paid to the recipient in (such as cash, check, money order, certified check, direct account deposit, etc.). Further, more information may be required to be collected by the money transfer operator by law based on the jurisdiction the money transfer transaction is being sent from or being sent to (e.g. identification of the persons involved, the purpose of the transaction, additional documentation, test question, etc.).

Before, after, or concurrently with the sender, agent, clerk and/or representative inputting information to the money transfer terminal, an imaging device may collect information from the sender. The imaging information may include all or a portion of financial information. The user may or may not be aware of this information or image being collected. Applicable law may or may not require the user be alerted as to the gathering of such information. The gathering of information with the imaging device may occur before the sender begins inputting information, while the user is inputting information, after the user has concluded inputting information, or any combination thereof.

The imaging device may analyze the information gathered from the user locally, or it may transfer raw or analyzed data to the money transfer terminal. The imaging device may also transfer raw or analyzed data to the host money transfer system directly or through the money transfer terminal. A transfer to the host money transfer system may include both the financial transaction information the sender has input or provided and the imaging information, or the imaging information and the financial transaction information may be transferred separately. In some embodiments, only imaging information is obtained and/or transferred (e.g., when imaging information includes financial transaction information).

At the host system, such imaging information may be analyzed by the host computer system, compared to profile information, compared to database information, and/or analyzed by an expert who has decision making authority on whether to allow the transaction or not or request additional information or documentation. Based on the imaging information and/or the transaction information, the sender may be required to submit more information, the transaction may be permitted, or the transaction may be blocked outright. To the sender, it may appear the transaction is proceeding normally even if the transaction has been blocked, so that the sender is not alerted to the fact that authorities have been alerted.

Imaging information may also be gathered when a recipient uses a money transfer terminal to receive the funds. The money transfer terminal may be the same or a different money transfer terminal than the terminal used by the sender. While the transfer may thus far have been approved through the money transfer system or required or permitted to continue by law enforcement authorities, based upon information entered by the recipient, or information gathered by an imaging device from the recipient, the money transfer transaction may be blocked, permitted, or more information may be required of the recipient.

Information about both the sender and the recipient may be compared to profiles of possible users and/or to other information maintained in one or more databases. For example, a profile may exist for a typical terrorist. The sender and the recipient may also be compared to information gathered about the same sender and/or recipient during previous transactions and/or registration (e.g., a user may have previously registered for loyalty programs, have conducted large principal transfers, registered through a webpage, etc.). The sender and recipient may also be compared against commercial, law enforcement, public, or other private databases containing information on possible users.

FIG. 1 illustrates a simplified block diagram of an example of a money transfer terminal 100. The money transfer terminal 100 may be a computer. The money transfer terminal may be operated by an agent or representative of the money transfer provider or by the sender or recipient (e.g. a home PC, kiosk, telephone, etc.). In some embodiments, the money transfer terminal includes: a data store 110, a processor 120, a telephone/microphone 130, a printer 140, a speaker 150, a keypad 160, an imaging interface device 170, a display screen 180, a scanner/card reader 190, and a network interface device 195. The money transfer terminal 100 may include a touch screen that functions as the display screen 180 and the keypad 160. The keypad 160 may instead be any device that accepts user input, such as a trackball, mouse, or joystick. The imaging interface device 170 may serve to allow the money transfer terminal 100 to communicate with the imaging device. Alternatively, an imaging device may be directly incorporated into the money transfer terminal 100. The speaker 150 may be any audio output device, such as headphones. The printer 140 may be used to provide the user a receipt, coupon, advertisement, or other information to be taken with her. The scanner 190 may be used to scan a barcode identifying a user or transaction, transaction identifier, a discount card, loyalty number, and/or a coupon. The telephone/microphone 130 may be used in conjunction with the speaker 150 to interact with the money transfer terminal 100, or a representative of the money transaction. The user and/or agent/clerk may contact, or be contacted by a customer service representative, or an expert who is evaluating whether to permit a money transfer transaction or not.

Figure 2:
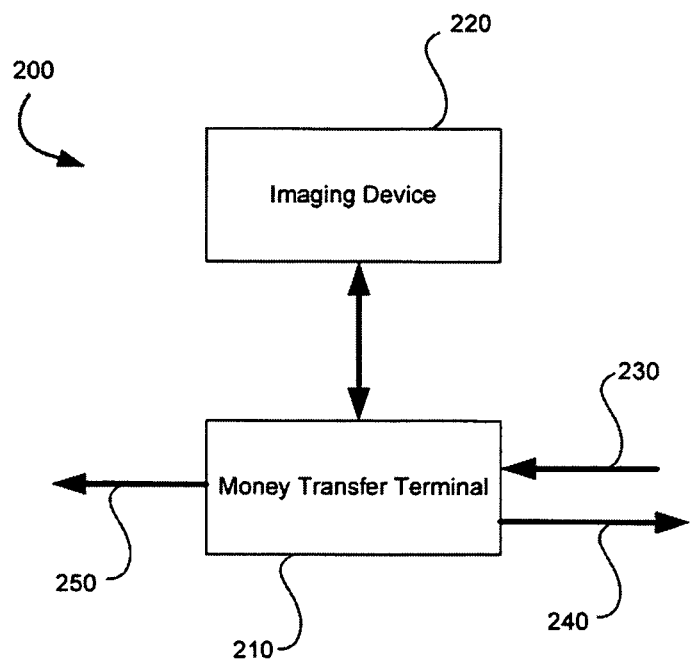
FIG. 2 is a simplified block diagram of an embodiment of a money transfer terminal with an imaging device.

FIG. 2 illustrates a simplified block diagram of a money transfer terminal with an imaging device 200. The money transfer terminal 210 may be the money transfer terminal 100 of FIG. 1, or may be a different money transfer terminal. The money transfer terminal 210 accepts user input 230 from user and/or agent/clerk. The user and/or agent/clerk may input such information as the sender's name, address, phone number, email address, loyalty number, and/or account number, the recipient's name, address, phone number, email address, and account number, the destination state or country, the sender's state or country (or some other expected payout location), the amount to be sent, the form the money will be paid to the money transfer operator, how soon the sender wants the money to be available to the recipient, and/or the form the money will be received by the recipient (such as cash, check, money order, directly into an account, etc.).

Additional information may be required by law or internal policy to be gathered from the sender (e.g., purpose of the transaction, test question/answer, additional documentation) or otherwise provided by sender or required by the money transfer provider.

The money transfer terminal 230 may output 240 to the user instructions, feedback, or other information based on the information received from the sender. The money transfer terminal 210 may output 250 information gathered from the sender after the sender has entered all pertinent information, during the information gathering process or at some future time. This information may be transmitted to a host money transfer system. The information may be transmitted electronically via a private network or a public network, such as the internet or the telephone network or a wireless network. This information may also be transmitted via a person, such as a courier or by voice over the telephone.

An imaging device 220 may be connected to the money transfer terminal. The imaging device may be alerted by the money transfer terminal 210 as to when to gather information from the sender. Alternatively, the imaging device 220 may independently determine when it is appropriate to gather information on the sender. The imaging device 220 may also be alerted by a host money transfer system as to when to gather information on the sender.

The imaging device 220 may gather many different types of information from the sender. For example, the imaging device may be a magnetic resonance imaging machine, capable of imaging the sender's brain and determining brain activity patterns. Brain activity patterns, which are neurons firing at varying intensities in different regions of the brain, may be used to determine what the sender is thinking about, what his state of mind is, and/or what his intention is for conducting the money transfer. The imaging device 220 may also be a camera or video camera, capable of detecting a sender's facial expressions. Based upon facial expressions, tics, or other movements, a determination of the user's motives and/or state of mind may be determined. The imaging device 220 may be used to take a picture or multiple pictures of the sender for comparison to a database of photographs of known criminals, suspects, terror watch list suspects, money launderers, persons of interest, credit fraud perpetrators or villains. The database may contain the same or similar information about sender from prior transactions. The imaging device 220 may gather a voice sample for voice recognition, conduct a retina scan, a fingerprint scan, etc. Each of these identifiers may be compared to information contained one or more internal or external databases.

In some embodiments, the imaging device 220 may include a functional MRI machine. A functional MRI may require the sender to remain still, or may allow a sender to maintain a normal amount of movement. The imaging device 220 may project a beam of light into the frontal cortex of the sender's brain. The reflected beam of light would then be analyzed to read complex thoughts, such as the sender's motives, state of mind, object of the money transfer, financial transaction information, etc.

An advanced brain scan with imaging device 220, such as with a functional MRI machine, would allow data entry by the sender to be conducted via the imaging device 220. For example, the sender may be able to input the sender's or recipient's name, sender's or recipient's address, sender's or recipient's telephone number, transaction information (e.g., amount being sent, receive destination, etc.), order information (e.g., good or service being purchased), financial transaction information, loyalty account information and/or any other piece of required and/or desired information though imaging of the sender's brain.

In some embodiments, the sender may or may not be aware that information is being captured of him via an imaging device 220. A non-surreptitious system may, for example, on the money transfer terminal 210, display an alert saying "Additional information about to be collected. Proceed?" The sender may then be given the chance to cancel the transaction and not have the imaging device 220 image him, or the sender may proceed with the financial transaction with the accompanying collection of information by the imaging device 220. In some embodiments, a warning may be displayed on the money transfer terminal 210 and/or on the imaging device 220 that imaging of the sender will occur if a money transaction is attempted to be completed. In some embodiments, the money transfer terminal 210 may present the sender with a question such as: "Is this money transfer intended for illegal, immoral, harmful or generally unscrupulous purposes?" While the question is being answered, before the question is answered, or after the question is answered, the imaging device may capture information to be analyzed whether or not the sender responds yes, no, or unknown.

Analysis of information captured by the imaging device 220 may be analyzed by the imaging device, it may be analyzed by the money transfer terminal 120, and/or it may be transmitted to a host system. The imaging device 120 may only selectively transmit information, or it may transmit all of the information it has received or processed to the money transfer terminal and/or the host system. In some embodiments, a determination is made at the imaging device whether the money transfer should be blocked, allowed, or additional information is required or desirable. In some embodiments, the veracity of information obtained through a terminal may be known based, at least in part, on the user image and/or imaging information. In other embodiments, a confidence score is determined to assess the likelihood that the information obtained through the terminal is true.

Figure 3:
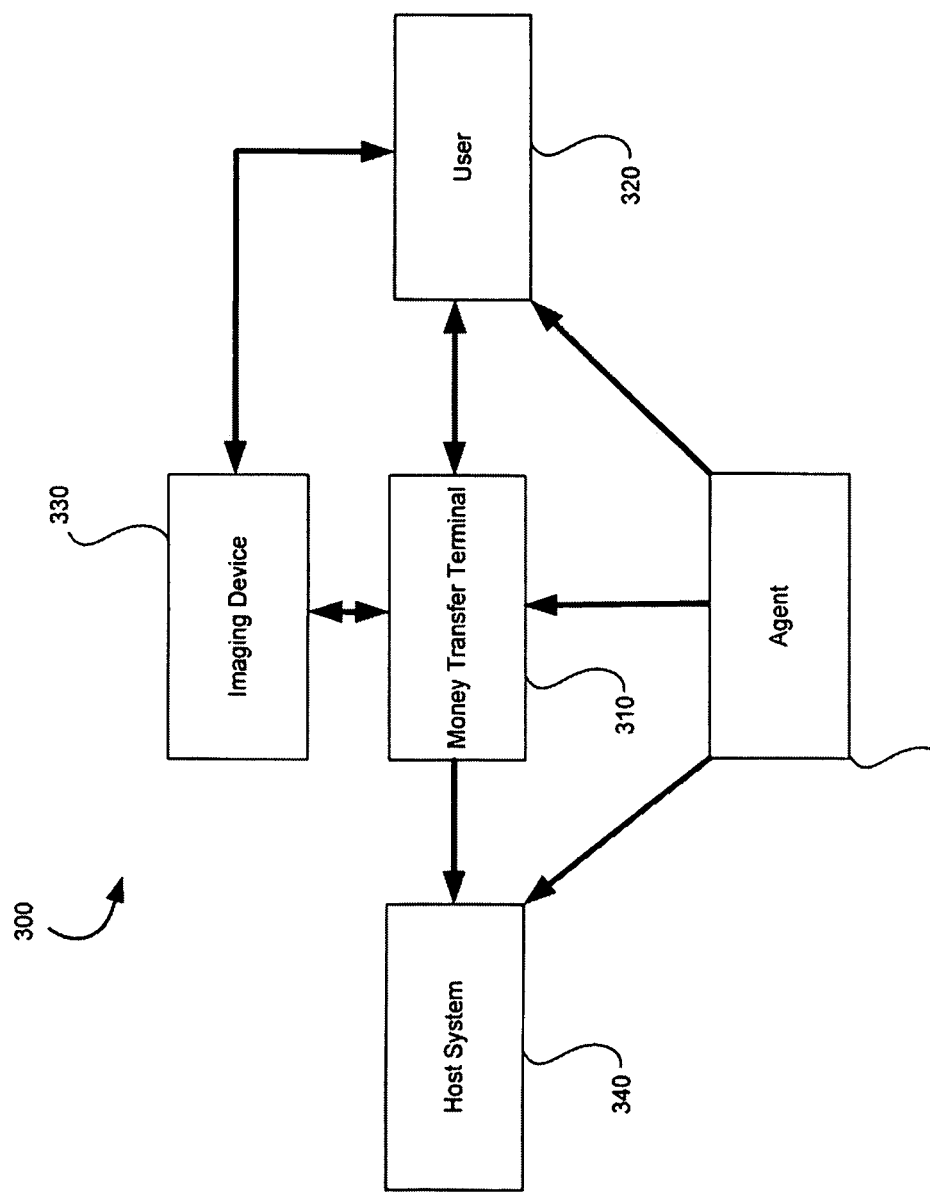
FIG. 3 is a simplified block diagram of another embodiment of a money transfer terminal with an imaging device connected to a host system.

In some embodiments, a money transfer terminal communicates with a host system. FIG. 3 shows a simplified block diagram of a money transfer system including an imaging device 300. The money transfer terminal 310 may be the money transfer terminal of FIG. 1 or FIG. 2, or it may be a different money transfer terminal. The money transfer terminal 310 of FIG. 3 receives information from the user 320, and outputs information to the user 320. The user 320 may be a sender, as previously described, or may be a recipient. The same or different information may be gathered for a recipient of funds as for a sender of funds. Information gathered from recipient may include the sender's name, where the money was sent from, and/or the expected payout amount.

The money transfer system 300 includes an imaging device. This may be the imaging device of FIG. 1, or it may be a different imaging device. Imaging device 330 may gather information from the user, such as through the methods and embodiments of the imaging device of FIG. 1, and may transmit such information to the money transfer terminal or the host system 340. In some embodiments, the imaging device 330 is integrated with the money transfer terminal 310, and is not a separate device or unit. Alternatively, the imaging device 330 may be a separate device or unit.

In FIG. 3, the user 320 interacts with the money transfer terminal 310 and with the imaging device 330. The money transfer terminal 310 may send information entered by the user 320 and/or the agent/clerk and imaging information gathered by the imaging device 330 to a host system 340. The host system may be a computer or a network of computers.

The host system 340 may be centralized or may be distributed over a large area, and may include storage devices, processors, network interfaces, displays, and databases. The host system 340 may store information entered by the user 320 and/or agent/clerk. The host system 340 may store information gathered by the imaging device 330, such as in a database. The information gathered by the imaging device 330 and the information entered by the user 320 and/or the agent/clerk may be stored in the same or different physical locations. They also may be stored in the same or different databases. In some embodiments, imaging information related to user 320 is deleted after a pre-determined period of time.

In some embodiments, no agent or representative of the money transfer system interacts directly with the user 320 or the money transfer terminal 310. In some embodiments, the agent may be an entity or a person employed by the entity, and the entity may or may not be licensed to provide money transfer or banking services. Alternatively, an agent 350 may interact with the user 320, the money transfer terminal 310, and the host system 340, or any combination thereof. For example, if the user 320 desires to pay or receive cash, the cash may be handed to or received from an agent 350 as opposed to being inserted into the money transfer terminal 310. The agent may then input to the money transfer terminal 310 that a certain amount of cash has been received or paid. Alternatively, the agent 350 or clerk may use a separate money transfer terminal, or may interact with the host system 340 to confirm that an amount of cash has been successfully received from or paid to the user 320. In some embodiments, the user may pay by credit card, debit card, prepaid card, gift card, money order, stored value card or account, such as a mobile wallet, or some combination thereof. Similar payment methods may be used for a payout to the user. These forms of payment or payout may be completed, in whole or in part, through imaging analysis.

In some embodiments, the agent 350 has the ability to provide additional information to supplement information gathered by the imaging device 330. Whether or not the user 320 is paying cash by other means or is otherwise required to interact with the agent 350, the agent may be able to associate information related to her personal observations of the user 320. For example, if while the user 320 is interacting with the money transfer terminal 310, the user 320 appears nervous, agitated, scared, wrathful, perspiring more than usual, or provides general evidence of devious behavior, the agent could input such information to the same money transfer terminal 310, a different money transfer terminal, or by another device which would result in such information being associated with the transaction being entered by the user 320. Such information may be provided before, during, and/or after the user 320 has completed the money transfer transaction. When a decision is being made as to whether to allow the transaction to proceed, the information provided by the agent 350 may be considered.

If after receiving information from the user and/or agent/clerk, either from the money transfer terminal 310 or the imaging device 330, or both, the user 320 and/or agent/clerk may be prompted to input additional information. For example, if the money transfer transaction is being made to an area known to be a hotbed of terrorist activities, such as Afghanistan, more information may be gathered by the imaging device 330 and more questions may be provided by the money transfer terminal 310 prior to the money transfer being permitted or evaluated. In some embodiments, the user 320 may be required to contact, such as by phone or in person, a representative of the money transfer company to answer questions and make assurances as to the legitimate nature of the money transfer.

Figure 4:
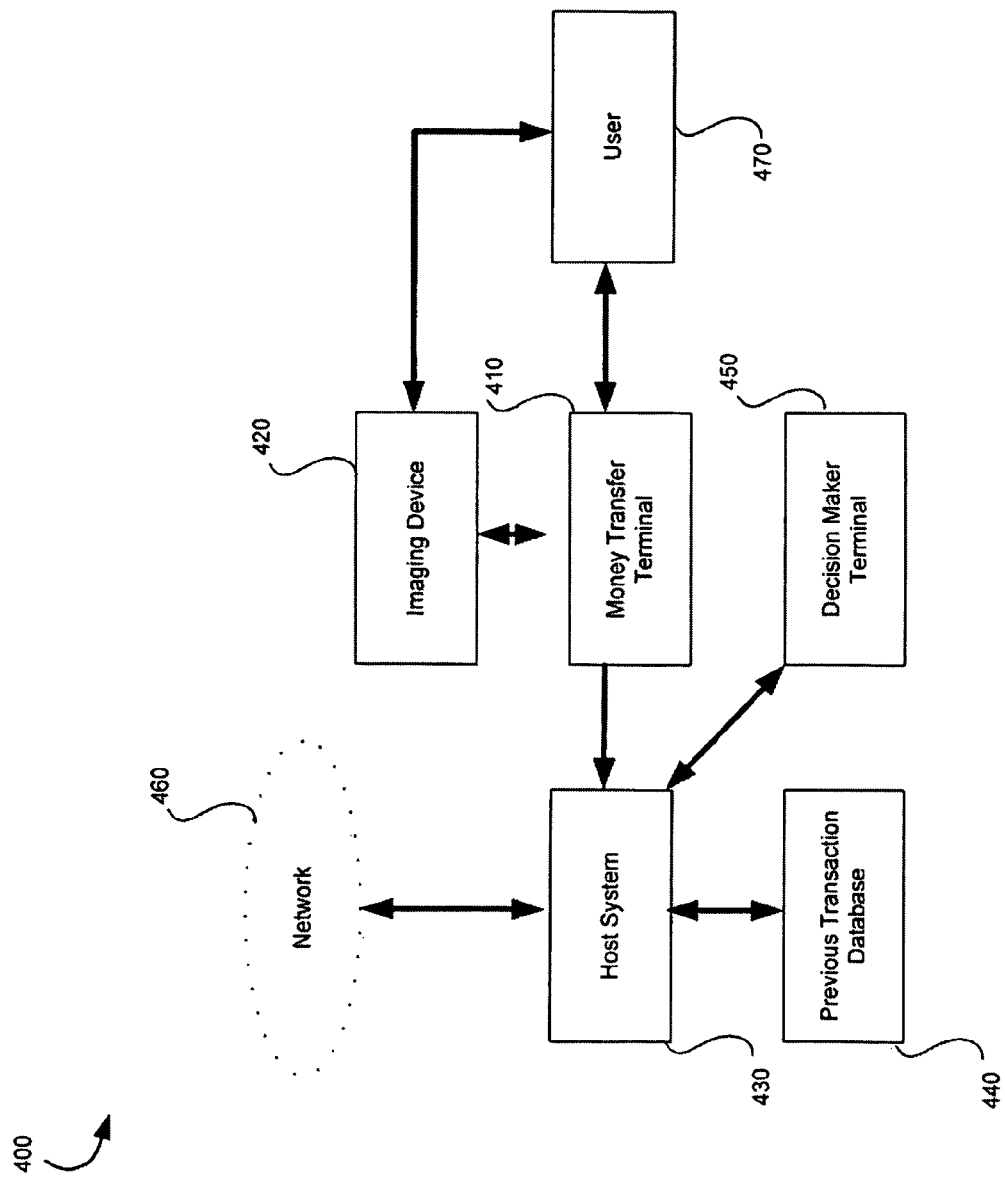
FIG. 4 is a simplified block diagram of another embodiment of a money transfer terminal with an imaging device and a previous transaction database.

The information received from the user may be analyzed many different ways. FIG. 4 illustrates a simplified block diagram of a money transfer system with an imaging device 400. In some embodiments, the money transfer system with an imaging device 400 includes: a money transfer terminal 410, an imaging device 420, a host system 430, a previous transaction database 440, a decision-maker terminal 450, and a network 460. The money transfer terminal 410, imaging device 420, and host system 430 may be the similarly named components of FIGS. 1-3, or they may be different.

FIG. 4 additionally illustrates a previous transaction database 440. This previous transaction database may be used to at least partially determine whether a money transfer should be permitted, blocked, or have more information gathered before reaching a decision. The previous transaction database may contain information regarding previous transactions conducted by the user 470. The user 470 may be a sender or recipient or both. While a money transfer transaction by the user 470 may not trigger the transaction being blocked for some number of times, it may eventually be blocked. For example, the user 470 may be permitted to send $500 to a recipient in Moscow. However, if the user 470 attempted to transmit another $500 to the same recipient, or a different recipient in the same region within a predetermined amount of time, the transaction may be blocked, or more information may be requested from the user 470 based upon information stored in the previous transaction database 440. A sender may be blocked from sending any transaction(s), or blocked from sending one or more transactions based on one or more criteria relating to the transaction or series of transactions (e.g., sending a number of transactions exceeding a predetermined number and/or amount in a predetermined amount of time, or to a predetermined number of different recipients). Instead of being completely blocked, transactions may be limited (e.g., send limits imposed, limits on corridors, etc.). The previous transaction database 440 may also be used to determine if transactions should be permitted to particular recipients. Based upon data stored in the previous transaction database 440, a recipient may be blocked from receiving transactions, receiving a number of transactions exceeding a predetermined number in a predetermined amount of time, or from a predetermined number of different senders. For example, a transaction sending $500 to a particular recipient may be permitted. However, if ten other transactions sending money to the same recipient within a week are noted in the previous transaction database 440, future transactions may be blocked or questioned.

FIG. 4 also illustrates a decision-maker terminal 450. In the illustrated embodiment, the decision-maker terminal is connected to the host system 430. The decision-maker terminal 450 may be used by a expert or designee of the money transfer system operator as to whether a particular money transfer or group of money transfer should be allowed to proceed. In some embodiments, the decision-maker terminal 450 includes an input device, a processor, a computer-readable storage device, a network connection, and a display device. The decision-maker, using the decision-maker terminal 450, may be presented an amount of information regarding a pending money transfer. The decision-maker terminal 450 may display information obtained with the imaging device 420, and information input by the user 470 and/or agent/clerk to the money transfer terminal 410. Additionally, the decision-maker terminal 450 may receive information noted by an agent during the process of a money transfer. The decision-maker, alternatively referred to as the expert, using the decision-maker terminal 450, may have the ability to at least partially determine whether a money transfer transaction should be permitted or blocked. The host system 430 may have the ability to make an initial determination of whether a money transfer should be permitted, blocked or requires additional information or documentation. The decision may then be forwarded to the decision-maker terminal 450 for review by the expert. In some embodiments, only blocked transactions are forwarded to the decision-maker terminal 450 for review by the expert. The expert, using the decision-maker terminal 450, may have the ability to override decisions made by the host system 430. In some embodiments, the host system 430 makes a recommendation as to whether to block the money transfer or not, with the decision-maker terminal 450 being used by the expert to make a final determination.

In some embodiments, the expert using the decision-maker terminal 450 has the ability to interact directly with user 470 and/or agent/clerk as the user and/or agent/clerk is interacting with the money transfer terminal 410. This may include sending additional questions to answer, calling the user 470 and/or agent/clerk via a telephone, or causing the imaging device 420 to collect more information on the user 470. The expert at the decision-maker terminal 450 may also flag the money transfer for a later determination of whether to allow or block based on information acquired from the recipient of funds. The existence of a decision-maker terminal 450 may be invisible to the user 470. The use of decision-maker terminal 450 may be concurrent with the information being entered by the user 470 and/or agent/clerk and/or may occur prior to the recipient receiving the funds. In some embodiments, the expert using the decision-maker terminal 450 has the ability to notify law enforcement via a network 460. In some embodiments, all decisions are made by the host system 430, with an expert using a decision-maker terminal 450 having the ability to override some or all of the decisions made by the host system.

The network 460 allows the host system 430 to interact with other systems. For example, the network may be a private network or virtual private network run by the money transfer system operator. The network may be used for communication between different host systems, or different money transfer terminals. Alternatively, the network 460 may be a public network, such as the Internet, and may allow the host system 430 to communicate with external systems and databases.

Figure 5:
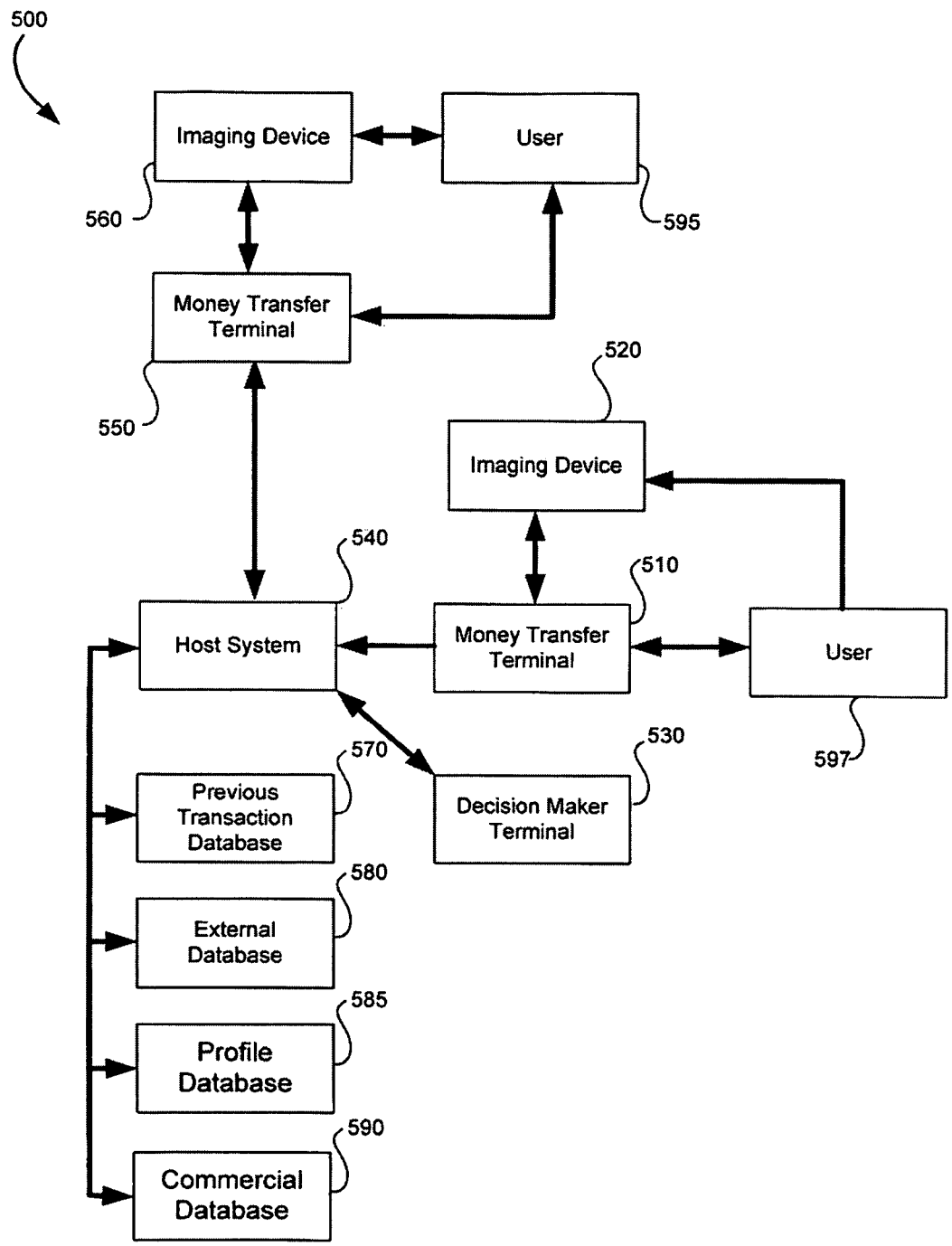
FIG. 5 is a simplified block diagram of another embodiment of a money transfer terminal with an imaging device and additional databases and a second money transfer terminal.

Additional databases may also be used to determine whether to permit, deny, or gather more information on a money transfer. FIG. 5 illustrates a simplified block diagram of a money transfer system with imaging capabilities 500. The embodiment of FIG. 5 includes a money transfer terminal 510, an imaging device 520, a decision-maker terminal 530, a host system 540, and a previous transaction database 570. These components may be the same as the similarly identified components of previous figures, or may represent other components.

Illustrated in FIG. 5 is a second money transfer terminal 550. This money transfer terminal may function identically to the other money transfer terminal 510. A user 597 may conduct a money transfer with money transfer terminal 510 either directly or through an agent/clerk, with another user 595, receiving the funds at the second money transfer terminal 550 either directly or through a agent/clerk. Imaging information may be gathered on the user 595 via a second imaging device 560. The imaging device 560 may or may not gather imaging information on user 595 based on information provided by user 597 to money transfer terminal 510, or information gathered by imaging device 520.

The embodiment of FIG. 5 further includes an external database 580. This external database may be maintained by a party separate from the money transfer system operator. For example, the external database 580 may be managed by a law enforcement agency. This database may contain information about suspected or known money launderers, criminals, terrorists, or other persons of interest. If a transaction is conducted by a person in this database, the transaction may be blocked or authorities may be alerted. In addition to containing information on particular persons, the external database 580 may contain profile information. For example, if the imaging device 520 or 560 receives information fitting a particular profile, such as a person exhibiting a particular list of characteristics, the money transfer may be blocked or delayed. Profile information may be maintained in one or more internal or external databases.

In some embodiments, a profile database 585 may be used to compare the sender or recipient to profiles of potential illegal users. For example, characteristics, including imaging data, may be compiled from one or more sources to create a profile of a potential terrorist. These characteristics may be compiled from real suspects, transactions and/or may be the result of research. A user exhibiting these characteristics may be blocked or questioned regarding the money transfer transaction.

The embodiment of FIG. 5 also includes a commercial database 590. A commercial database 590 may be maintained by a company, such as a credit agency, or data mining agency. Information in the commercial database 590 may be maintained and updated by the money transfer system operator, or by some other entity. The commercial database may be stored at the host system 540, or may be external to the host system 540, but accessible by the host system 540.

Decisions as to whether to permit, block, and/or obtain additional information about a money transfer and/or user may be dependent on more than one single factor. For example, while information collected from the imaging device 520 or 560 signals a possible illegal transfer, information in the databases 570, 580, and/or 590 may prove otherwise. In some embodiments, a specific weight may be assigned to each information source, for example, information from the previous transaction database 570 may receive 20% of the decision making weight, with imaging information from the imaging device receiving 50% weight, and the remainder divided between the external database 580 and the commercial database 590. In some embodiments, no definite weight may be assigned to each source of information, with the decision left up to an expert using the decision-maker terminal 530.

Figure 6:
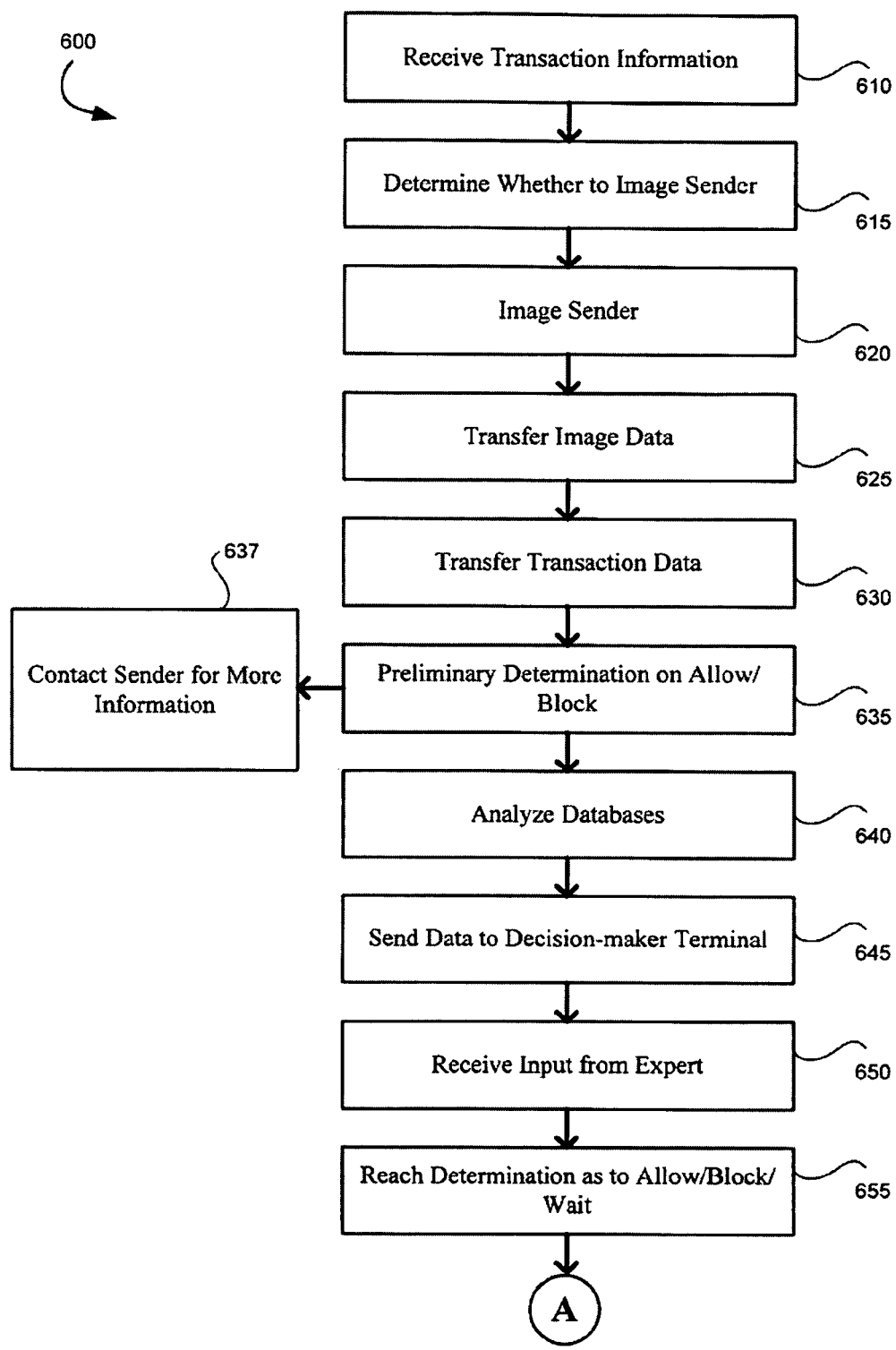
FIG. 6 is a simplified block diagram of a method of conducting a money transfer with a sender.

The systems and devices of FIGS. 1-5 may be used to execute a method of using an imaging analysis to determine whether to permit, block, or obtain additional information about a money transfer and/or user. FIG. 6 illustrates an exemplary embodiment of a method for determining whether to permit a sender to complete a money transfer 600. As those with skill in the art will understand, many of the stages described herein may be rearranged into a different order without impacting the purpose of the method. First, transaction information is received 610. This may include information about the sender, the recipient, the financial transaction, and both the sender's and receiver's motives and/or intentions.

Based upon information received from the sender, a determination 615 may be made at the imaging device, the money transfer terminal, and/or the host system whether imaging of the sender and/or recipient is necessary or desired. In some embodiments, if the transaction appears highly innocuous, such as a one-time transfer of $100 to a family member, the sender may not be imaged at all. Conversely, if the sender conducts a large number of transactions involving thousands of dollars, it may be required for the sender to be imaged. Imaging may be required by law or internal policy. Imaging may or may not required the prior consent of the user. Next, the sender is imaged 620. The imaging of the sender 620 may include taking one image, or multiple images. The image may be a photograph or video, or may be subcutaneous. The step of imaging the sender 620 may or may not include asking the sender if he or she agrees to be imaged. If he or she does not agree, the money transfer may be cancelled or delayed.

Next, the image data may be transferred 625 to either the host system or the money transfer terminal. Similarly, the transaction data may be transferred 630 to the host system or to another money transfer terminal. The image data and the transaction data may be transferred together or separately to the host system.

Based upon the image data and/or the transaction data a determination on whether to allow, deny, or request more information 635 is made. This decision may be made at the host system, the money transfer terminal, a decision-maker terminal, and/or an imaging device. This determination 635 may be preliminary. For example, the determination may be made to temporarily allow the transaction, but re-evaluate the transaction after comparisons are made in databases, or the recipient is imaged and investigated. In some embodiments, the preliminary determination may be a final decision. For example, if the imaging information reveals a high probability of illegality of the transaction, the transaction may be blocked outright, with the authorities alerted. In some embodiments, a decision to block or re-evaluate the transaction at a later time may lead to the sender being contacted 637 for more information regarding the transaction, her motives, her background, her citizenship, or any other information relevant to the transaction.

Following the preliminary determination 635, databases, such as the commercial databases, external databases, and/or previous transaction databases, may be analyzed 640. In some embodiments, the databases may only be analyzed if certain information is present in the imaging data collected or the transaction data collected. Alternatively, the database information may be analyzed before imaging to determine whether the sender should be imaged.

Next, all or part of the analyzed data may be sent to a decision-maker terminal 645 for an expert to review. The expert may decide outright that the transaction should be blocked, he may flag for further review, or he may permit the transaction to proceed. The expert's decision is input 650 to the decision-maker terminal. Alternatively, he may only be allowed to give an opinion, with the host system or a money transfer terminal making the final determination.

Following the decision by the expert, another determination may be made. At this point a determination may be made to block or allow the transaction 655 or obtain additional information and/or documentation. Again, the determination may be contingent on information received later on from the recipient of the funds. In some embodiments, the determination has been made to allow the transaction no matter the results of the imaging of the recipient. A determination may also be made at this time not to image the recipient at all. The method continues as depicted in FIG. 7 with the recipient receiving the funds intended for him.

Figure 7:
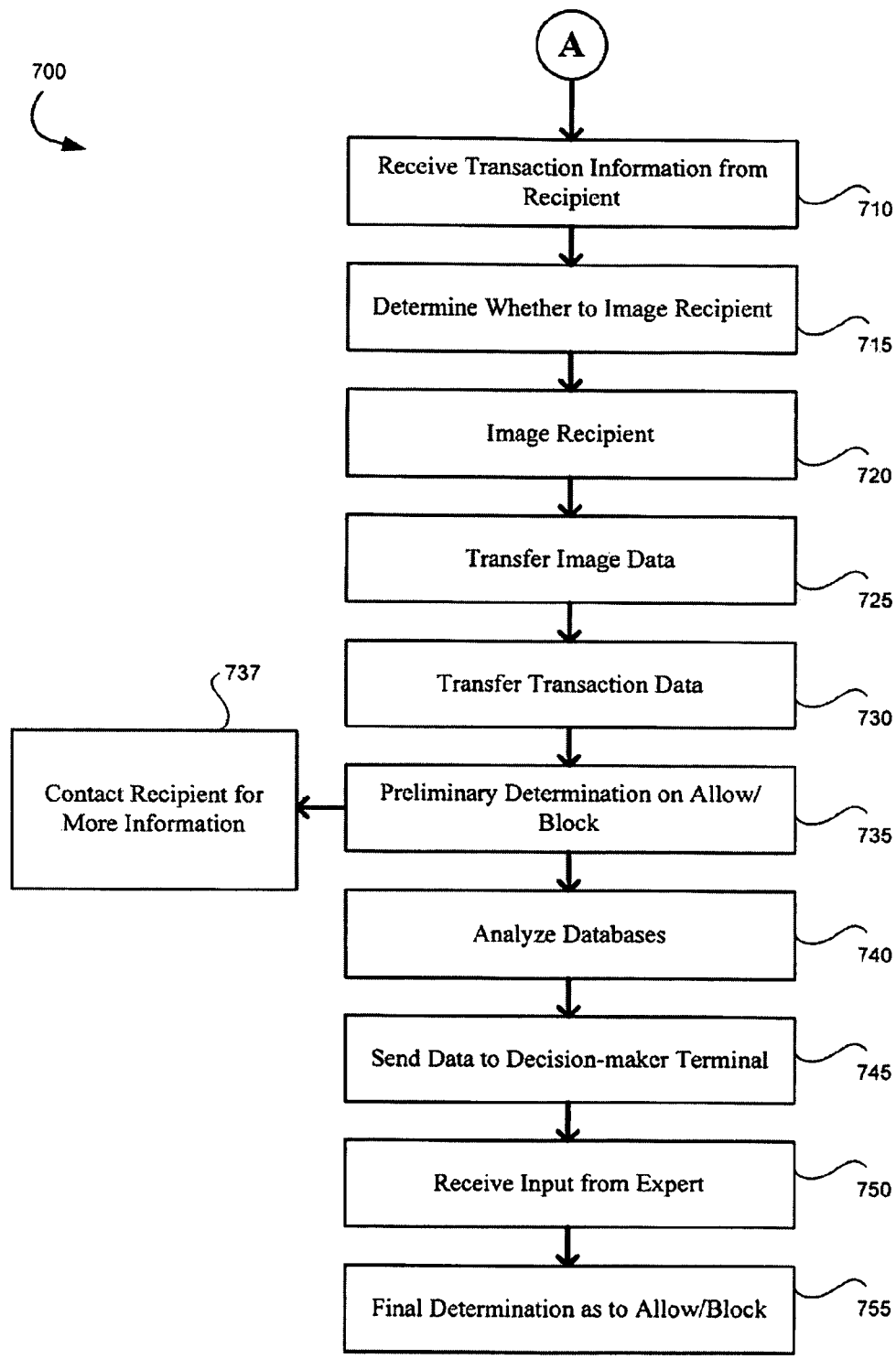
FIG. 7 is a simplified block diagram of a method of conducting a money transfer with a recipient.

FIG. 7 illustrates a simplified block diagram of a method for issuing funds sent by a sender to a recipient 700. The method may be regarded as a continuation of the sending process illustrated in FIG. 6, or as a separate process or method. First, transaction information is received from the recipient 710 and/or agent/clerk at a money transfer terminal. The transaction information may be in the form of a barcode to scan, a transaction number, the recipient's name address, and/or phone number, the sender's name, address, or phone number, the anticipated payout amount, or any information capable of identifying the sender, recipient, or transaction.

Based upon this information, or information previously received or analyzed regarding the sender, a determination as to whether to image the recipient 715 is made. In some embodiments, the recipient may always or never be imaged.

If the recipient is to be imaged, one or multiple images of the recipient are taken 720. Following the collection of the image or images, image data is transmitted 725 to the money transfer terminal and/or the host system. Transaction data entered by or relating to the recipient may also be transmitted 730 to the host system, at the same time, before, or after the image data is transmitted.

At this point a determination may be made as to whether to allow, block, or gather more information on a transaction 735 and/or user. This determination may be final, or may be a preliminary determination. Depending on the information received from the recipient, the recipient may be contacted for more information 737. For example, an expert may call the recipient and/or sender and ask him further questions.

Before funds are released to the recipient or the transaction is denied, databases may be analyzed for data on the recipient 740. If the recipient was previously identified by the sender in a method similar to that of FIG. 6, a search of the databases for the recipient may already have been conducted. Information may then be sent to a decision-maker terminal 745 to receive input from an expert 750. This may result in a transaction that has previously been evaluated by an expert, being reevaluated by the same or a different expert. In some embodiments, the expert at this stage has a greater amount of information presented to him because the recipient has also entered or provided information and possibly been imaged.

Prior to dispensing the funds to the recipient, a final determination of whether to allow or block the transaction or obtain additional information and/or documentation may be made 755. In some embodiments, the transaction may be allowed, but information about the transaction is forwarded to a government agency. In some embodiments, a transaction is maintained in a pending state until a further investigation of the parties involved may be conducted.

Merely by way of example, the host systems may be one or more servers. These servers may be a web server, which can be used, merely by way of example, to process requests from the imaging devices and/or money transfer terminals. The web server can also run a variety of server applications, including HTTP servers, FTP servers, CGI servers, database servers, Java™ servers, and the like. In some embodiments of the invention, the web server may be configured to serve web pages that can be operated within a web browser on the money transfer terminal or the imaging device to perform methods of the invention.

Merely by way of example, the server(s) can be one or more general purpose computers capable of executing programs or scripts in response to the money transfer terminals and/or imaging devices and/or other servers, including without limitation web applications (which might, in some cases, be configured to perform methods of the invention). Merely by way of example, a web application can be implemented as one or more scripts or programs written in any suitable programming language, such as Java™, C, C# or C++, and/or any scripting language, such as Perl, Python, or TCL, as well as combinations of any programming/scripting languages. The application server(s) can also include database servers, including without limitation those commercially available from Oracle™, Microsoft™, Sybase™, IBM™ and the like, which can process requests from clients (including, depending on the configuration, database clients, API clients, web browsers, etc.) running on the money transfer terminals, imaging devices and/or another server. In some embodiments, an application server can create web pages dynamically for displaying the information in accordance with embodiments of the invention. Data provided by an application server may be formatted as web pages (comprising HTML, Javascript, etc., for example) and/or may be forwarded to the money transfer terminals and/or imaging devices via a web server (as described above, for example). Similarly, a web server might receive web page requests and/or input data from the money transfer terminals and/or imaging devices and/or forward the web page requests and/or input data to an application server. In some cases, a web server may be integrated with an application server.

In accordance with further embodiments, one or more servers can function as a file server and/or can include one or more of the files (e.g., application code, data files, etc.) necessary to implement methods of the invention incorporated by an application running on a money transfer terminals and/or imaging devices and/or another server. Alternatively, as those skilled in the art will appreciate, a file server can include all necessary files, allowing such an application to be invoked remotely by a another computer and/or server. It should be noted that the functions described with respect to various servers herein (e.g., application server, database server, web server, file server, etc.) can be performed by a single server and/or a plurality of specialized servers, depending on implementation-specific needs and parameters.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

While the specification has focused on money transfers, such systems and methods may be applied to a wide variety of financial transactions if an imaging device is available, such as ATM transactions, bank withdrawals and deposits, financial transactions on the internet Instead of a money transfer terminal, a computer with a webcam, a mobile video device, a cellular phone with a built-in camera, or any similar suitable device may be used.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

Further, the application refers to certain persons alternatively as "he" or "she." This does not serve as a limitation on the gender of the identified party.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A method of processing a money transfer comprising:
   providing a money transfer system comprising a money transfer terminal, an imaging device, a host computer system, and a decision maker terminal;
   receiving, at the money transfer terminal, financial transaction information from a user relating to a money transfer requested by the user;
   acquiring, with the imaging device, a magnetic resonance imaging (MRI) image of the user;
   receiving, at the money transfer terminal from the imaging device, the MRI image;
   presenting, with the money transfer terminal, a question to the user regarding the money transfer;
   receiving, at the money transfer terminal from the imaging device, a first additional MRI image of the user prior to presentation of the question, a second additional MRI image of the user during presentation of the question, and a third additional MRI image of the user after presentation of the question;
   transmitting, from the money transfer terminal to the host computer system, the financial transaction information and the MRI image;
   transmitting, from the money transfer terminal to the host computer system, the first additional MRI image, the second additional MRI image, and the third additional MRI image;
   retrieving, by the host computer system, MRI imaging information associated with a previous financial transaction by the user;
   transmitting, from the host computer system to the decision-maker terminal, the financial transaction information, the MRI image, and the MRI imaging information associated with the previous financial transaction;
   transmitting, from the host computer system to the decision-maker terminal, the first additional MRI image, the second additional MRI image, and the third additional MRI image;
   evaluating, with the decision-maker terminal, the financial transaction information;
   comparing, with the decision-maker terminal, the MRI image with the MRI imaging information associated with the previous financial transaction;
   determining, with the decision-maker terminal, based at least in part on the evaluation of the financial transaction information and the comparison of the MRI image with the MRI imaging information associated with the previous financial transaction, whether to approve the money transfer, wherein determining, with the decision-maker terminal, whether to approve the money transfer is further based at least in part on a comparison between at least two of the first additional MRI image, the second additional MRI image, or the third additional MRI image;

transmitting, from the decision-maker terminal to the host computer system, an indication of whether the money transfer is approved; and transmitting, from the host computer system to the money transfer terminal, the indication of whether the money transfer is approved.

2. The method for processing a money transfer of claim 1 further comprising:

receiving, at a second money transfer terminal, a request from a recipient to disburse funds associated with the money transfer;

acquiring, from a second imaging device, an MRI image of the recipient;

receiving, at the second money transfer terminal from the second imaging device, the MRI image of the recipient;

transmitting, from the second money transfer terminal to the host computer system, the request and the MRI image of the recipient;

retrieving, by the host computer system, MRI imaging information associated with a previous financial transaction by the recipient;

transmitting, from the host computer system to the decision-maker terminal, the request, the MRI image of the recipient, and the MRI imaging information associated with the previous financial transaction by the recipient;

evaluating, with the decision-maker terminal, the request;

determining, with the decision-maker terminal, based at least in part on the evaluation of the request and the comparison of the MRI image of the recipient with the MRI imaging information associated with the previous financial transaction by the recipient, whether to approve the request;

transmitting, from the decision-maker terminal to the host computer system, an indication of whether the request is approved; and transmitting, from the host computer system to the money transfer terminal, the indication of whether the request is approved.

3. The method for processing a money transfer of claim 1 further comprising:

receiving, at the decision-maker terminal, a decision by an expert of whether the user has an illegal purpose for the money transfer, wherein the decision is based upon a presentation of the MRI image to the expert; and wherein determining, with the decision-maker terminal, whether to approve the money transfer is further based at least in part on the decision by the expert of whether the user has an illegal purpose for the money transfer.

4. A method of processing a money transfer comprising:

providing a money transfer system comprising a money transfer terminal, an imaging device, a host computer system, and a decision maker terminal;

receiving, at the money transfer terminal, financial transaction information from a user relating to a money transfer requested by the user;

determining, with the money transfer terminal, based at least in part on the financial transaction information received from the user, that the money transfer requested by the user requires MRI imaging of the user to approve the transaction;

acquiring, with the imaging device, a magnetic resonance imaging (MRI) image of the user;

receiving, at the money transfer terminal from the imaging device, the MRI image;

transmitting, from the money transfer terminal to the host computer system, the financial transaction information and the MRI image;

retrieving, by the host computer system, MRI imaging information associated with a previous financial transaction by the user;

transmitting, from the host computer system to the decision-maker terminal, the financial transaction information, the MRI image, and the MRI imaging information associated with the previous financial transaction;

evaluating, with the decision-maker terminal, the financial transaction information;

comparing, with the decision-maker terminal, the MRI image with the MRI imaging information associated with the previous financial transaction;

determining, with the decision-maker terminal, based at least in part on the evaluation of the financial transaction information and the comparison of the MRI image with the MRI imaging information associated with the previous financial transaction, whether to approve the money transfer;

transmitting, from the decision-maker terminal to the host computer system, an indication of whether the money transfer is approved; and transmitting, from the host computer system to the money transfer terminal, the indication of whether the money transfer is approved.

* * * * *